United States Patent [19]

Morikawa et al.

[11] Patent Number: 5,453,537
[45] Date of Patent: Sep. 26, 1995

[54] METHOD FOR PREPARING AN N-PHOSPHONOMETHYLGLYCINE

[75] Inventors: Kohei Morikawa; Sumio Soya, both of Kawasaki; Hidejiro Yokoo, Chiba, all of Japan

[73] Assignee: Showa Denko K.K., Tokyo, Japan

[21] Appl. No.: 260,959

[22] Filed: Jun. 16, 1994

Related U.S. Application Data

[62] Division of Ser. No. 961,363, Oct. 15, 1992, Pat. No.5,324,855.

[30] Foreign Application Priority Data

Oct. 17, 1991 [JP] Japan ................... 3-269584

[51] Int. Cl.$^6$ ................................................. C07F 9/38
[52] U.S. Cl. ................................................. 562/17
[58] Field of Search ................................................. 562/17

[56] References Cited

U.S. PATENT DOCUMENTS

| | | | |
|---|---|---|---|
| 4,486,358 | 12/1984 | Moser | 260/502.5 |
| 4,534,904 | 8/1985 | Moser | 260/502.5 |
| 4,670,191 | 6/1987 | Kleiner | 260/502.5 |
| 5,068,404 | 11/1991 | Miller et al. | 502/17 |

FOREIGN PATENT DOCUMENTS

| | | |
|---|---|---|
| 370992A | 5/1990 | European Pat. Off. . |
| 2422675 | 11/1979 | France . |
| 1142294 | 2/1969 | United Kingdom . |

OTHER PUBLICATIONS

Derwent 92–378211; Oct. 5, 1992.

*Primary Examiner*—José G. Dees
*Assistant Examiner*—Samuel Barts
*Attorney, Agent, or Firm*—Sughrue, Mion, Zinn, Macpeak & Seas

[57] ABSTRACT

The invention is directed to a process for preparing N-phosphonomethylglycine comprising the steps of reacting an aminomethylphosphonic acid with a glyconitrile in the presence of an alkali metal hydroxide to form a product, and then hydrolyzing the product by adding an alkali metal hydroxide in an amount sufficient to neutralize the resulting carboxylic acid.

8 Claims, No Drawings

METHOD FOR PREPARING AN N-PHOSPHONOMETHYLGLYCINE

This is a divisional of application Ser. No. 07/961,363 filed Oct. 15, 1992 now U.S. Pat. No. 5,324,855.

BACKGROUND OF THE INVENTION

1. Field of the Invention

The present invention relates to a method for preparing an N-acylaminomethylphosphonic acid useful as an intermediate for synthesizing N-phosphonomethylglycine known as the herbicide glyphosate.

2. Description of Prior Art

Reaction between an N-methylolamide compound and a phosphorus trihalide to prepare an N-acylaminomethylphosphonic acid or aminomethylphosphonic acid has been known by itself and can roughly be classified into 1) a process in which the reaction proceeds without solvents; 2) a process in which the reaction proceeds in an organic solvent; and 3) a process in which the reaction proceeds in an organic acid.

However, the known processes have various defects as described below and are practically disadvantageous.

For example, 1) as for the process without solvents, a process is disclosed in Synthetic Communication, vol. 16, No. 7, p.733, in which process N-methylolbenzamide is added to a mixture of phosphorus trichloride and trimethylphosphite for reaction to obtain O,O'-dimethyl-N-phosphonomethylbenzamide in a yield of 79%, which then is hydrolyzed to prepare amiomethylphosphonic acid. This process is economically disadvantageous since it uses a large amount of trimethylphosphite, which is relatively expensive. Also, Sb. Vys. Sk. Chem.-Technol. Praze. Org. Chem. Technol., C28, p.115 discloses a process in which aminomethylphosphonic acid is prepared from N-methylolformamide and phosphorus trichloride in the absence of solvents. This process gives a very low yield as low as 29.5%, which is practically unacceptable.

U.S. Pat. Nos. 2,328,358 and 2,304,156 disclose processes in which various N-methylolamide compounds and phosphorus trihalides are reacted in the absence of solvents, and then brought into contact with excess of water to obtain amiomethylphosphonic acid. However, the examples therein use long reaction times ranging 1 to 4 days with low yields. As to the yield of the objective compounds, only the yield of the reaction using N-methylolstearylamide, 62%, was recited but nothing was described about the other reactions. Afterwards, referring to this U.S. patent, J. Pract. Chem., vol. 329, No. 1, p.19 pointed out that the yield of N-acylaminomethylphosphonic acid before the hydrolysis of the amide was 20% to 35%.

As described above, the reactions in the absence of solvents not only have various disadvantages that they generally must use relatively expensive raw materials in excessive amounts, the reaction times are long, yields are low, and so on, but also they suffer difficulty in control since they use phosphorus trihalides which makes them exothermic reactions. Thus, the solventless reactions are in no way practical.

2) As for the process in which reaction proceeds in an organic solvent, examples which use carbon tetrachloride, ethyl acetate, acetic acid or the like are described in U.S. Pat. Nos. 2,328,358 and 2,304,156 referred to above. Although accurate evaluation is impossible because no concrete yield values were shown in those U.S. patents, one skilled in the art might expect no great differences with respect to the long reaction time and low yield from those in the case of solventless reactions.

In U.S. Pat. No. 2,304,156, explanation is made to the effect that the reaction proceeds in two stages: first, an N-methylolamide compound is reacted with phosphorus trichloride in the absence of solvents or in an organic solvent to prepare dichlorophosphorus ester ($RCONHCH_2OPCl_2$), which then is converted to aminomethylphosphonyl dichloride ($RCONHCH_2POCl_2$) by a rearrangement reaction, and the latter compound is reacted with water to give rise to N-acylaminomethylphosphonic acid [$RCONHCH_2PO(OH)_2$]. However, none of these intermediates has been isolated from the reaction mixture and put to determination of the chemical structure. Among the aforementioned reactions, the rearrangement reaction from dichlorophosphorus ester to phosphonyl dichloride is said to take a long time as long as on the order of day.

Reportedly, the low reaction rate could be improved by elevating the reaction temperature, or by addition of a small amount of a weak acid such as acetic acid, propionic acid or acetic anhydride. However, the present inventors have found that the effect of increasing yield by these attempts is insufficient. For example, when N-methylolacetamide and phosphorus trichloride were reacted for 24 hours at room temperature and then the reaction mixture was brought in contact with a large amount of water, the yield of the resulting N-acetylaminomethylphosphonic acid was found to be 32%. When the reaction was continued for 3 hours with elevating the reaction temperature to 90° C., the yield of N-acetylaminomethylphosphonic acid was 38% and it was only a slight improvement. When the reaction proceeded for 3 hours at 90° C. after addition of acetic acid, the yield was 65% at a ratio of acetic acid to phosphorus trichloride being 1.5 times molar amount, and 63% at a ratio of acetic acid to phosphorus trichloride being even 10 times molar amount. Thus, improvements, if any, were insufficient. While the reasons why the yield is low are unclear, one possible reason may be that N-methylolamide is splitted to methylenediamide and formaldehyde in contact with phosphorus trichloride although the present inventors do not want to be bound thereto.

3) The processes in which the reaction proceeds in an organic acid, particularly the one which uses acetic acid, exhibit relatively higher yields among the known processes, and hence most of recently proposed processes relate to improvement of such processes.

For example, Synthesis, 1989, No. 4, p.547 discloses a process in which N-methylolbenzamide or 1,3,5-triacetylhexahydro- 1,3,5-triazine is reacted with phosphorus trichloride in acetic acid to prepare N-acylaminomethylphosphonic acid, which is then hydrolyzed after acetic acid and acetyl chloride are distilled off from the reaction mixture to obtain aminomethylphosphonic acid. However, it is reported that sufficient results can be obtained only when aromatic starting compounds are used and that nitrilotrismethylphosphonic acid is a major product when aliphatic starting compounds are used.

European Patent 370,992 discloses a process in which after treating acetamide and paraformaldehyde in a nonaqueous system containing acetic acid, phosphorus trichloride is added thereto for reaction to prepare N-acetylaminomethylphosphonic acid, which is then hydrolyzed to obtain aminomethylphosphonic acid after distilling off the solvent and by-products from the reaction mixture. Polish Patent 117,780 discloses a process in which N-methylolbenzamide is reacted with phosphorus trichloride in acetic acid, the resulting N-benzoylaminomethylphosphonic acid is hydrolyzed to prepare aminomethylphosphonic acid.

These processes involving the reactions in acetic acid solvents exhibit relatively higher yields than the other known processes but on the other hand, acetyl halides are by-produced and hence additional efforts are needed in order to separate and collect them as well as acetic acid as the solvent, which leads to economical disadvantage.

SUMMARY OF THE INVENTION

Accordingly, an object of the present invention is to provide a process for preparing an N-acylaminomethylphosphonic acid from an N-methylolamide compound and a phosphorus trihalide which process solves the defects of the known process and provide an industrially advantageous process that can exhibit high yield, is easy to control the reaction, is simple in the separation of the objective compound from the reaction mixture, and so on.

According to the process of the present invention, the above-described object is achieved as follows. Firstly use is made of a solvent with view to making it easy to control the reaction in view of the fact that N-methylolamides and phosphorus trihalides which inherently are highly reactive (chemically unstable) compounds are used and the reaction itself is an exothermic reaction; secondly aprotic solvent is selected as the solvent making the use of advantage of not producing by-products derived from the solvent itself and being separated and collected without difficulty; and thirdly, particularly as a measure for increasing the yield of N-acylaminomethylphosphonic acid, which is a main purpose, water in a predetermined amount relative to the phosphorus trihalide is added and the reaction is proceeded for several hours with heating at 60° to 160° C., followed by contacting the reaction mixture with water.

That is, according to the present invention, there is provided a process for preparing an N-acylaminomethylphosphonic acid, comprising the steps of:

mixing an N-methylolamide compound with a phosphorus trihalide in an aprotic solvent in the presence of water in a 0.25 to 2.5 times molar amount relative to the phosphorus trihalide and heating the resulting reaction mixture at 60° to 160° C.; and contacting the reaction mixture with water.

DETAILED DESCRIPTION OF THE INVENTION

Hereafter, the process of the present invention will be described in detail.

The N-methylolamide compound used as one of the starting compounds in the process of the present invention includes N-methylol-lower alkylamides and N-methylolarylamides. Representative examples thereof include N-methylolformamide, N-methylolacetamide, N-methylolpropionamide, N-methylol-(t-,i- or n-)butyramide, N-methylol-(i- or n-)valeramide, N-methylolbenzamide, N-methylol-(o-, m- or p-)toluamide, N-methylol-(o-, m- or p-)ethoxybenzamide, N-methylol-(o-, m- or p-)chlorobenzamide, N-methylol-(2,3-, 2,4-, 2,5-, 2,6-, 3,4- or 3,5-)dimethoxybenzamide, N-methylol-3,4,5-trimethoxybenzamide, etc. From these, corresponding N-acylaminomethylphosphonic acid can be obtained, respectively. As the phosphorus trihalide, phosphorus trichloride, phosphorus tribromide, phosphorus triiodide, etc. can be used. From practical viewpoint, phosphorus trichloride is preferred.

The solvent is not limited particularly, and any solvents can be used in the process of the present invention so far as they are stable, do not decompose or react with the starting compounds under the reaction conditions, and can dissolve N-methylolamides and phosphorus trihalides, the starting compounds, uniformly. Usually, aprotic solvents such as hydrocarbons, halogenated hydrocarbons, ethers, polyethers, nitriles, and aromatic nitro compounds are used. Representative examples of them include methylcyclopentane, cyclohexane, hexane, 2-methylpentane, 3-methylpentane, methylcyclohexane, heptane, 2-methylhexane, 3-methylhexane, 2,3-dimethylpentane, 2,4-dimethylpentane, ethylcyclohexane, octane, 2,2,3-trimethylpentane, 2,2,4-trimethylpentane, nonane, 2,2,5-trimethylhexane, decane, decahydronaphthalene, benzene, toluene, xylene, ethylbenzene, isopropylbenzene, mesitylene, butylbenzene, cumene, propyl ether, isopropyl ether, butyl ether, ethylbutyl ether, pentyl ether, isopentyl ether, 1,2-dimethoxyethane, diglyme, tetrahydrofuran, 1,4-dioxane, tetrahydropyran, benzyl ethyl ether, anisole, phenetole, fluorobenzene, fluorotoluene, chlorobutane, chloropentane, chlorobenzene, chloroform, carbon tetrachloride, dichloroethane, trichloroethane, dichloroethylene, pentachloroethane, dichlorobenzene, nitrobenzene, acetonitrile, propionitrile, etc. Among these, propyl ether, isopropyl ether, butyl ether, ethyl butyl ether, pentyl ether, isopentyl ether, 1,2-dimethoxyethane, diglyme, 1,4-dioxane, benzyl ethyl ether, anisole, phenetole, etc. are preferred from practical viewpoints of solubilities of the starting compounds therein, ease of separation and collection after the reaction, economical advantage, etc.

Molar proportion of N-methylolamide and phosphorus trihalide, the starting compounds, at the initiation of the reaction may in principle be 1:1 which is stoichiometric but either one of the starting compounds can be used in a slight excess. In this case, it is preferred from practical viewpoint to use the phosphorus trihalide in an about 1.0 to 1.5 times molar amount, particularly an about 1.05 to 1.3 times molar amount, relative to the N-methylolamide.

One of the most important requirements of the process of the present invention is to add a predetermined amount of water to the mixture of the starting compounds at the initiation of the reaction and the conditions therefor. That is, the addition of water to the solution of N-methylolamide and phosphorus trihalide gives an important influence to the yield of the objective compound, and the yield also depends largely on the amount of water added. For example, when water was added to a mixed solution of N-methylolacetamide and phosphorus trichloride kept at 20° C. on a water bath in a varied amount, the mixture was reacted for 3 hours after elevating the temperature to 90° C., and then contacted with a large amount of water, followed by determination of the yield of N-acylaminomethylphosphonic acid, the yield gradually increased with increased amount of water, i.e., the yield was about 50% for 0.25 time molar amount, about 60% for 0.5 time molar amount, about 70% for 1.0 time molar amount, about 85% for 1.25 times molar amount, and about 85% for 1.5 times molar amount, of water with respect to phosphorus trichloride while the yield was about 40% without addition of water. However, the amount of water added exceeded a certain level, the yields gradually decreased such as about 70% for 1.75 times molar amount, about 60% for 2.0 times molar amount and about 50% for 2.5 times molar amount, of water with respect to phosphorus trichloride. Therefore, the amount of water added is generally about 0.25 to 2.5 times molar amount, preferably about 0.5 to 2.0 times molar amount, and more preferably about 1.0 to 1.8 times molar amount, of water with respect to phosphorus trihalide.

Incidentally, when the reaction was carried out using acetic acid in place of water, the yield of N-acylaminomethylphosphonic acid was about 62% for 1.0 time molar amount, about 65% for 1.5 times molar amount, about 64% for 2.0 times molar amount, and about 63% for 10 times molar amount, of acetic acid with respect to phosphorus trichloride. Thus the yield was by about 20% lower than the case where water was used, which means contribution to the increase of the yield of the objective compound is considerably poor by the use of acetic acid.

The addition of water must be performed as soon as possible after the preparation of the mixed solution of N-methylolamide and phosphorus trihalide, the starting compounds. It is undesirable for the N-methylolamide and the phosphorus trihalide to be kept in a mixed state for long time because by-products tend to occur due to the reaction therebetween even at low temperatures. There will be substantially no difference in the yield regardless of whether water is added to the mixed starting solution of the N-methylolamide and the phosphorus trihalide or a mixture of the N-methylolamide and water is added to the phosphorus trihalide. On the other hand, when the phosphorus trihalide is added to a mixture of N-methylolamide and water, the yield of the objective compound is not so high as the former case.

As stated above, the amount of water to be added in the initial stage of the reaction contributes to the increase in the yield greatly, and the yield varies depending on the order of mixing the N-methylolamide, the phosphorus trihalide and water. While the reason therefor is unclear, it may be presumed that unlike the reaction route described in the aforementioned U.S. patents, the reaction mechanism of the process of the present invention in which water is copresent is as follows. That is, first certain active phosphorus halide compounds, for example, hydroxyphosphorus halides are produced from the phosphorus trihalide and water, and the compounds react with the N-methylolamides to produce N-acylaminomethylphosphonyl halides, which then are hydrolyzed with a large amount of water to give rise to N-acylaminomethylphosphonic acid. The production of certain active phosphorus halide compounds from phosphorus trichloride and water is described, for example, in Compt. Rend., vol. 232, p. 2443; and Docl. Akad. Nauk. SSSR, vol. 268, No. 2, p.364.

The temperature of the starting compounds when they are mixed with each other gives a great influence to the yield of the objective compound, and therefore constitutes one of the important requirements of the process of the present invention. That is, either when the mixed solution of the starting compounds, i.e., the N-methylolamide and the phosphorus trihalide is prepared and water added thereto, or when a mixed solution of the N-methylolamide and water is added to the phosphorus trihalide, the mixing of the starting compounds must be carried out at temperatures not exceeding 60° C. Preferably, the reaction may proceed at temperatures Within the range of between 0° to 30° C. Incidentally, while it is needless to say that the contact between water or a system containing water with the phosphorus trihalide has to be carried out at temperatures as low as possible, it must be avoided to mix the N-methylolamide with the phosphorus trihalide at temperatures above 60° C. since in that case they react vigorously to produce a methylenebisamide compound as a main product and polymers of phosphorus and the like as well. It is thus desirable to prepare a mixed solution of the starting compounds and elevate the temperature of the reaction mixture as soon as possible after the addition of water.

While there are no precise limitations posed on the reaction conditions but at reaction temperatures of lower than 60° C., the reaction takes a long time during which undesirable side reactions could occur while at reaction temperatures higher than 200° C., it will be difficult to control the reaction appropriately. Therefore, it is suitable to carry out the reaction at temperatures generally within the range of between 60° C. and 200° C., and preferably within the range of 70° C. and 120° C. The reaction pressure may be either subatmospheric or superatmospheric but usually, the reaction may proceed under atmospheric pressure. While it depends on the reaction temperature, a reaction time of about 1 to 5 hours may be sufficient.

After completion of the first stage of the reaction, the reaction mixture is cooled, and then the solvent is removed by decantation, thereafter distilling off under reduced pressure or the like to give a slurry, which then is contacted with water to complete the hydrolysis of N-acylaminomethylphosphonyl halide to N-acylaminomethylphosphonic acid. While there are no precise limitations posed on the reaction conditions in this stage, suitably the amount of water to be added is in a 10 to 30 times molar amount with respect to the phosphorus trihalide used as one of the starting compounds, the reaction temperature is between room temperature and 60° C., the reaction time is about 0.5 to 3 hours.

In the both first and second stages, the reaction may be practiced either by a batch process or a continuous process.

N-Acylaminomethylphosphonic acid, the reaction product, can be isolated with ease, for example, by removing water and the reaction solvent followed by crystallization from an appropriate solvent such as methanol.

Aminomethylphosphonic acid can be prepared without difficulty by hydrolyzing the N-acylaminomethylphosphonic acid prepared by the process of the present invention. The hydrolysis reaction can be performed with ease by the use of either mineral acids such as sulfuric acid and hydrochloric acid or alkali metal hydroxides such as sodium hydroxide and potassium hydroxide. However, when the alkali metal hydroxides are used, the products are in the form of alkali metal salts and thus it is necessary to neutralize in order to obtain aminomethylphosphonic acid. The hydrolysis of N-acylaminomethylphosphonic acid is performed, for example, under the conditions of 60° C. for about 5 hours. The starting compound, i.e., N-acylaminomethylphosphonic acid may be provided after it is isolated from the reaction product in the preceding stage and purified but crude product just after removal of the reaction solvent may also be used directly.

Preparation of N-Phosphonomethylglycine

Next, explanation will be made on the preparation of N-phosphonomethylglycine using aminomethylphosphonic acid as a starting compound.

As for the process for preparing N-phosphonomethylglycine using aminomethylphosphonic acid as a starting compound, various processes are known including, for example, a process in which aminomethylphosphonic acid is added to an aqueous solution of glyoxal at 40° to 45° C. followed by heating the mixture as disclosed in Japanese Patent Application Laid-Open No. 61992/1987; a process in which aminomethylphosphonic acid and glyoxal, starting compounds, are reacted in the presence of sulfur dioxide as disclosed in European Patent 81,459 and U.S. Pat. No. 4,369,142; a process in which aminomethylphosphonic acid and glyoxylic acid are reacted and thereafter reduced with hydrogen in the presence of palladium catalyst as described in European Patent 186,648; a process in which aminomethylphosphonic acid and chloroacetic acid are heated to about 80° to 120° C. in the presence of an acid acceptor such as sodium hydroxide as described in Polish Patent 120,759 and Spanish Patent 504,479; and a process in which aminomethylphosphonic acid and diethyl bromomalonate are reacted under alkaline conditions, and then hydrolyzed under acidic conditions using sulfuric acid as described in Spanish Patent 545,456. These process, however, are unsatisfactory in one way or another since they use gases which are difficult to handle, the reactions are complicated in the operation, the yields of the reactions are insufficient, and so on.

Furthermore, U.S. Pat. No. 4,221,583 discloses a process for preparing N-phosphonomethylglycinonitrile or its monosalts in which aminomethylphosphonic acid is reacted with formaldehyde optionally in the presence of an alkali necessary for preparing its monosalt to convert aminomethylphosphonic acid to N-methylol derivative, which is then reacted with potassium cyanide at pH 7 to 10. This patent also discloses the preparation of N-phosphonomethylglycine by the hydrolysis of the thus obtained N-phosphonomethylglycinonitrile. However, according to the examples in that patent the yield of N-phosphonomethylglycinonitrile was at most 66%, and it was necessary to use a large excessive amount such as 2.4 times molar amount of potassium cyanide with respect to aminomethylphosphonic acid in order to increase the conversion of aminomethylphosphonic acid. The yield of hydrolysate of N-phosphonomethylglycinonitrile was at most 90% according to the examples in that patent, resulting in that the yield of N-phosphonomethylglycine based on aminomethylphosphonic acid was about 60%.

As a result of extensive investigation by the present inventors on the process for preparing N-phosphonomethylglycine using aminomethylphosphonic acid as a starting compound, it has now been confirmed that the objective compound can be obtained efficiently by reacting aminomethylphosphonic acid and glycolonitrile with adding an alkali metal hydroxide in such an amount that the aminomethylphosphonic acid can be converted to its corresponding dialkali metal salt, and then hydrolyzing the product by the use of an alkali metal hydroxide in an amount enough to neutralize the resulting carboxylic acid therewith.

That is, after reacting aminomethylphosphonic acid and glycolonitrile in the presence of an alkali metal hydroxide at a temperature not exceeding 60° C., the product is hydrolyzed with adding an alkali metal hydroxide in an amount enough to neutralize the resulting carboxylic acid, thereby obtaining N-phosphonomethylglycine in a high yield.

More specifically, the addition of the alkali metal hydroxide in the reaction of aminomethylphosphonic acid and glycolonitrile is because aminomethylphosphonic acid is an amphoteric compound which has both an amino group and a phosphono group in the same molecule and because it is necessary for the amino group in the aminomethylphosphonic acid to have a non-ionized form so that aminomethylphosphonic acid and glycolonitrile can react with each other.

In other words, when at least one of the two hydroxyl groups in the aminomethylphosphonic acid, that give acidity, is not neutralized with the alkali metal hydroxide, a portion or almost all of the amino groups of aminomethylphosphonic acid molecules are in the form of ions, i.e., so-called amphoteric ions, as observed generally in amphoteric compounds, and they do not react with glycolonitrile. As will be understood from this, it is preferred that at least 2 times molar amount of the alkali metal hydroxide be added to aminomethylphosphonic acid. While the molar proportion of the alkali metal to aminomethylphosphonic acid is not so strict, when the alkali metal hydroxide is added excessively to such an extent that there is a large amount of substantially free alkali metal hydroxide, the yield decreases as a result of decomposition of glycolonitrile and on the other hand, when the amount of the alkali metal hydroxide is too small, the reactivity of aminomethylphosphonic acid decreases for the reasons set forth above, which also leads to reduction in the yield. Therefore, it is suitable to add the alkali metal hydroxide within the range centering at two times molar amount with allowance of ±0.5 time molar amount, i.e., within the range of 1.5 to 2.5 times molar amount, preferably 1.8 to 2.2 times molar amount, with respect to aminomethylphosphonic acid.

Preferred examples of the alkali metal hydroxide include sodium hydroxide and potassium hydroxide.

The amount of glycolonitrile used in the reaction may preferably be stoichiometric, i.e., equimolar, with respect to aminomethylphosphonic acid so far as the amount of he alkali metal hydroxide is within the aforementioned range with respect to aminomethylphosphonic acid. This amount is not so strict either. However, when the amount of glycolonitrile is relatively larger than the amount of aminomethylphosphonic acid, the excessive glycolonitrile causes side reactions and on the other hand, when the former is smaller than the latter, aminomethylphosphonic acid, which is relatively expensive, remains unused. Therefore, it is preferred to avoid both the extremities. For the reasons above, it is suitable to add the glycolonitrile within the range centering at equimolar amount with allowance of ±0.5 time molar amount, i.e., within the range of 0.5 to 1.5 times molar amount, preferably 0.8 to 1.2 times molar amount, with respect to aminomethylphosphonic acid. The pH of the reaction mixture varies depending upon the charge amounts of the starting compounds and the reaction temperature and no particular limitation is posed thereon strictly, it is 10.5 or more when the reaction proceeds under the aforementioned conditions.

The manner of the reaction is not limited particularly, and usually an aqueous solution of glycolonitrile is added to a stirred mixed aqueous solution of aminomethylphosphonic acid and an alkali metal hydroxide, and the resulting mixture is further stirred to complete the reaction.

The temperature at which the reaction between aminomethylphosphonic acid and glycolonitrile is performed is desirably not exceeding 60° C. When the reaction temperature is too high, side reactions occur, thus decreasing the yield. On the other hand, too low a reaction temperature decreases the reaction rate. Usually, suitable reaction temperature is 0° to 60° C., preferably 10° to 40° C.

Reaction time varies depending upon the reaction temperature but it is suitably within the range of between about 30 minutes and 3 hours.

The amount of the alkali metal hydroxide added at the time of hydrolysis must be one enough to neutralize therewith the resulting carboxylic acid by hydrolysis. When the amount of the alkali metal hydroxide is less than necessary, the hydrolysis would not proceed, and on the contrary, when it is excessive, the amount of its salt formed upon isolation of N-phosphonomethylglycine by precipitation with an acid increases. Therefore, it is desirable to avoid the both extremities. The temperature of the hydrolysis reaction is not limited particularly but usually the hydrolysis reaction proceeds at temperatures between 60° C. and the boiling point of the reaction mixture. The reaction time, which depends on the reaction temperature, may usually be within the range of about 1 to 3 hours. When the reaction is carried out at temperatures below the boiling point of the reaction mixture, it is desirable to boil the reaction mixture at least once before the reaction is over in order to remove ammonia produced during the hydrolysis reaction.

N-Phosphonomethylglycine can readily be isolated by precipitation with an acid from the reaction mixture thus obtained, after dilution or concentration, if desired. Alternatively, the product can be isolated and purified by using other known means such as ion exchange resin singly or in combination with another, or further purified by recrystallization.

According to the process for preparing N-phosphonomethylglycine by reacting aminomethylphosphonic acid with glycolonitrile under the aforementioned conditions, N-phosophonomethylphsophonic acid can be obtained with ease at high yield. In other words, the conversions of aminomethylphosphonic acid and glycolonitrile are 95% or more, respectively, and the selectivity of N-phosphonomethylglycine amounts to 95% or more.

In the example of U.S. Pat. No. 4,221,583, it is described to the effect that the conversion of aminomethylphosphonic acid was 80% when aminomethylphosphonic acid and formamide were reacted in the presence of sodium hydroxide in a 1.3 times molar amount with respect to aminomethylphosphonic acid to convert aminomethylphsophonic acid to N-methylol form, followed by adding potassium cyanide in a 1.1 times molar amount with respect to aminomethylphosphonic acid with keeping pH between 8 to 9 using an aqueous hydrochloric acid solution. It is apparent that the process in which glycolonitrile is used but formation of N-methylol derivative of aminomethylphosphonic acid is not involved is more advantageous than the aforementioned known process. Further, under the reaction conditions at pH 8 to 9 as described in the aforementioned U.S. patent, even when glycolonitrile is produced from unused formaldehyde and potassium cyanide present in the reaction system, apparently the reaction of glycolonitrile with aminomethylphosphonic acid fails to occur as described above, the process of the invention in which aminomethylphosphonic acid and glycolonitrile are reacted under the conditions sufficient for the reaction to proceed, that is, under the conditions under which an alkali metal hydroxide is added in a 1.5 to 2.5 times molar amount with respect to aminomethylphosphonic acid, and at a pH of 10.5 or higher is a process unique enough to be thought of from the disclosure in the U.S. patent.

EXAMPLES

Hereafter, the process of the present invention will be described in more detail by representative working examples and reference examples, which are merely exemplary, and the invention should in no way be construed as being limited thereto.

Example 1

In a 300 ml flask on a water bath kept at 20° C. was charged a solution of 45.32 g (0.33 mole) of phosphorus trichloride in 40 ml of diglyme, to which solution was then dropwise added a solution of 27.11 g (0.30 mole) of N-methylolacetamide in 30 ml of diglyme, with stirring so that the temperature the whole reaction system did not exceed 30° C. Then, a solution of 8.10 g (0.45 mole) of water in 20 ml of diglyme was added dropwise similarly to the above aqueous solution with stirring so that the temperature did not exceed 30° C. After completion of the dropwise addition, the flask was heated on an oil bath to 100° C., and stirred for 5 hours for reaction.

After completion of the reaction, the reaction mixture was cooled down to room temperature to form two layers, and the upper layer was removed by decantation, and 100 ml of water was added to the remaining solution and the mixture was stirred at room temperature for 30 minutes, followed by distilling off the solvent under reduced pressure to obtain N-acylaminomethylphosphonic acid. The yield was found to be 89% by liquid chromatographic analysis.

Examples 2 to 16

The procedures in Example 1 were repeated using various starting compounds, solvents and reaction conditions for the first stage, and the results obtained are shown in Table 1. In Table 1, the following abbreviations are used, and the reaction conditions shown relate to the first stage only and the reaction in the second stage was the same as in Example 1.

Starting Compound

MAA: N-Methylolacetamide
MPA: N-Methylolpropionamide
MBA: N-Methylolbenzamide
MMA: N-Methylol-4-methoxybenzamide Product N-Acetylaminomethylphosphonic acid
PAMP: N-Propionylaminomethylphosphonic acid
BAMP: N-Benzoylaminomethylphosphonic acid
MBAMP: N-(4-Methoxybenzoyl)aminomethylphosphonic acid

TABLE 1

| | N-Methylol-amide (mole) | Phosphorus trihalide (mole) | Amount of water (mole) | | Reaction Condition | | Result of Reaction | |
|---|---|---|---|---|---|---|---|---|
| Example | | | | Solvent | Reaction temperature | Reaction time | Product | Yield |
| 2 | MAA | PCl₃ | 0.16 | Dioxane | 100° C. | 3 hours | AAMP | 52% |

TABLE 1-continued

| Example | N-Methylolamide (mole) | Phosphorus trihalide (mole) | Amount of water (mole) | Solvent | Reaction temperature | Reaction time | Result of Reaction Product | Yield |
|---|---|---|---|---|---|---|---|---|
| 3 | MAA 0.30 | PCl$_3$ 0.33 | 0.33 | Dioxane | 100° C. | 3 hours | AAMP | 69% |
| 4 | MAA 0.30 | PCl$_3$ 0.33 | 0.50 | Dioxane | 100° C. | 3 hours | AAMP | 83% |
| 5 | MAA 0.30 | PCl$_3$ 0.33 | 0.56 | Dioxane | 100° C. | 3 hours | AAMP | 62% |
| 6 | MPA 0.30 | PCl$_3$ 0.33 | 0.50 | Dioxane | 100° C. | 3 hours | PAMP | 84% |
| 7 | MBA 0.30 | PCl$_3$ 0.33 | 0.50 | Dioxane | 100° C. | 3 hours | BAMP | 86% |
| 8 | MMBA 0.30 | PCl$_3$ 0.33 | 0.50 | Dioxane | 100° C. | 3 hours | MBAMP | 81% |
| 9 | MAA 0.30 | PCl$_3$ 0.33 | 0.50 | Dimethoxy-ethane | 120° C. | 2 hours | AAMP | 85% |
| 10 | MAA 0.30 | PCl$_3$ 0.33 | 0.50 | Heptane | 90° C. | 3 hours | AAMP | 77% |
| 11 | MAA 0.30 | PCl$_3$ 0.33 | 0.50 | Carbon tetra-chloride | 70° C. | 5 hours | AAMP | 75% |
| 12 | MAA 0.30 | PCl$_3$ 0.33 | 0.50 | Nitro-benzene | 120° C. | 1 hour | AAMP | 73% |
| 13 | MAA 0.30 | PBr$_3$ 0.33 | 0.50 | Diglyme | 100° C. | 3 hours | AAMP | 88% |
| 14 | MBA 0.30 | PBr$_3$ 0.33 | 0.50 | Diglyme | 100° C. | 3 hours | BAMP | 85% |
| 15 | MAA 0.30 | PCl$_3$ 0.30 | 0.45 | Dioxane | 100° C. | 3 hours | AAMP | 80% |
| 16 | MAA 0.30 | PCl$_3$ 0.36 | 0.54 | Dioxane | 100° C. | 3 hours | AAMP | 86% |

Reference Example 1

In a 200 ml, four-necked flask equipped with a stirrer, a thermometer, a dropping funnel and a reflux condenser was charged a mixture of 50 g of water, 16.7 g of a 48% aqueous sodium hydroxide solution (200 mmol), and 11.1 g of aminomethylphosphonic acid (100 mmol), which mixture then was stirred. The pH of the mixture then was 13.1 as measured using a pH meter corrected with a buffer solution of pH 7 at 20° C. (hereafter, the same).

An aqueous 14.3 g of 40% glycolonitrile solution (100 mmol) was dropwise added to the reaction mixture in 30 minutes while cooling the reaction vessel in ice water to keep the temperature of the reaction mixture therein at a temperature not exceeding 5° C. After completion of the dropwise addition, the resulting mixture was stirred at a temperature not exceeding 5° C. for 30 minutes and then the temperature was elevated back to room temperature, followed by stirring at that temperature for 1 hour. The pH of the reaction mixture then was 11.0.

Next, 8.4 g of an aqueous 48% sodium hydroxide solution (100 mmol) was added, and the resulting mixture was heated under reflux for 2 hours. After completion of the reaction, the reaction mixture was subjected to analysis by high performance liquid chromatography (HPLC), which revealed that the reaction mixture contained 94 mmol of N-phosphonomethylglycine. The yield was 94% based on aminomethylphosphonic acid and glycolonitrile, the starting compounds.

After neutralizing it to pH 2 with concentrated hydrochloric acid, the reaction mixture was left to stand for one night to precipitate N-phosphonomethylglycine, which was then filtered. After washing with water and drying, the crystals of N-phosphonomethylglycine weighed, 13.4 g. Its purity determined by HPLC was 98%. The yield from aminomethylphosphonic acid and glycolonitrile, the starting compounds, was 78%.

Reference Example 2

The procedures of Reference Example 1 were repeated except that the temperature of the reaction mixture at the time of dropwise addition of glycolonitrile was kept at about 20° C., and after completion of the dropwise addition the resulting mixture was stirred for 1 hour at about 20° C. Analysis by HPLC of the reaction mixture after the reaction was over revealed that the yield of N-phosphonomethylglycine was 95% based on aminomethylphosphonic acid and glycolonitrile, the starting compounds.

Reference Example 3

The procedures of Reference Example 1 were repeated except that the temperature of the reaction mixture at the time of dropwise addition of glycolonitrile was kept at about 60° C., and after completion of the dropwise addition the resulting mixture was stirred for 1 hour at about 60° C. Analysis by HPLC of the reaction mixture after the reaction was over revealed that the yield of N-phosphonomethylglycine was 72% based on aminomethylphosphonic acid and glycolonitrile, the starting compounds.

Reference Example 4

In an apparatus similar to that used in Reference Example 1 was charged a mixture of 50 g of water, 8.4 g of an aqueous 48% sodium hydroxide solution (100 mmol) and 11.1 g of aminomethylphosphonic acid (100 mmol), which was then stirred. The pH of the mixture then was 9.7.

An aqueous 14.3 g of 40% glycolonitrile solution (100 mmol) was dropwise added to the reaction mixture in 30 minutes while cooling the reaction vessel in ice water to keep the temperature of the reaction mixture therein at a temperature not exceeding 5° C. After completion of the dropwise addition, the resulting mixture was stirred at a temperature not exceeding 5° C. for 30 minutes and then the temperature was elevated back to room temperature, followed by stirring at that temperature for 1 hour. The pH of the reaction mixture then was 9.5. Analysis by HPLC of the reaction mixture revealed that the conversions of aminomethylphosphonic acid and glycolonitrile, starting compounds, was 5% or less.

Next, 8.4 g of an aqueous 48% sodium hydroxide solution was dropwise added in 15 minutes. The pH after completion of the addition was 11.2. The reaction mixture was stirred as it was at 20° C. for 1 hour. The reaction mixture was analyzed by HPLC, which revealed that the conversions of aminomethylphosphonic acid and glycolonitrile, the starting compounds, were 95% or more, respectively.

Then, 8.4 g of an aqueous 48% sodium hydroxide solution (100 mmol) was added and the resulting mixture was heated under reflux for 2 hours. After completion of the reaction, the reaction mixture was subjected to analysis by HPLC. This revealed that the yield was 91% based on aminomethylphosphonic acid and glycolonitrile, the starting compounds.

What is claimed is:

1. A process for preparing N-phosphonomethylglycine, comprising the steps of:

reacting an aminomethylphosphonic acid with a glycolonitrile in the presence of an alkali metal hydroxide to form a product, and then hydrolyzing said product by adding alkali metal hydroxide in an amount sufficient to neutralize a resulting carboxylic acid.

2. The process as claimed in claim 1, wherein the reaction of the aminomethylphosphonic acid with the glycolonitrile is carried out at a temperature not exceeding 60° C.

3. The process as claimed in claim 1, wherein the reaction of the aminomethylphosphonic acid with the glycolonitrile is carried out at a pH of 10.5 or more.

4. The process as claimed in claim 1, wherein the glycolonitrile is used in an amount of about 0.5 to 1.5 times molar amount relative to the aminomethylphosphonic acid.

5. The process as claimed in claim 1, wherein the alkali metal hydroxide is used in an amount of about 1.5 to 2.5 times molar amount relative to the aminomethylphosphonic acid.

6. The process as claimed in claim 1, wherein the alkali metal hydroxide is sodium hydroxide or potassium hydroxide.

7. The process as claimed in claim 1, wherein the process comprises hydrolyzing an N-acylaminomethylphosphonic acid to produce the aminomethylphosphonic acid before said reacting step.

8. The process as claimed in claim 7, wherein the N-acylaminomethylphosphonic acid is made by mixing an n-methylolamide compound with a phosphorus trihalide in an aprotic solvent in the presence of water in a 0.25 to 2.5 times molar amount relative to the phosphorus trihalide and heating the resulting reaction mixture with water.

* * * * *